United States Patent [19]

Fukudome et al.

[11] Patent Number: 5,852,171

[45] Date of Patent: Dec. 22, 1998

[54] CLONING AND REGULATION OF AN ENDOTHELIAL CELL PROTEIN C/ ACTIVATED PROTEIN C RECEPTOR

[75] Inventors: Kenji Fukudome; Charles T. Esmon, both of Oklahoma City, Okla.

[73] Assignee: Oklahoma Medical Research Foundation, Oklahoma City, Okla.

[21] Appl. No.: 878,283

[22] Filed: Jun. 18, 1997

Related U.S. Application Data

[62] Division of Ser. No. 289,699, Aug. 12, 1994, Pat. No. 5,695,993.

[51] Int. Cl.⁶ .................................................. C07K 14/705
[52] U.S. Cl. ........................................... 530/350; 530/380
[58] Field of Search ...................................... 530/350, 380

[56] References Cited

PUBLICATIONS

Ecke et al. *Agents & Actions, Supp.*, vol. 38, pp. 182–189 (Abstract Only), 1992.

*Primary Examiner*—Paula K. Hutzell
*Assistant Examiner*—Stephen Gucker
*Attorney, Agent, or Firm*—Arnall Golden & Gregory, LLP

[57] ABSTRACT

Human protein C and activated protein C were shown to bind to endothelium specifically, selectively and saturably (Kd=30 nM, 7000 sites per cell) in a $Ca^{2+}$ dependent fashion. Expression cloning revealed a 1.3 kb cDNA that coded for a novel type I transmembrane glycoprotein capable of binding protein C. This protein appears to be a member of the CD1/MHC superfamily. Like thrombomodulin, the receptor involved in protein C activation, the endothelial cell protein C receptor (EPCR) function and message are both down regulated by exposure of endothelium to TNF. Identification of EPCR as a member of the CD1/MHC superfamily provides insights into the role of protein C in regulating the inflammatory response, and determination of methods for pharmaceutical use in manipulating the inflammatory response.

5 Claims, 10 Drawing Sheets

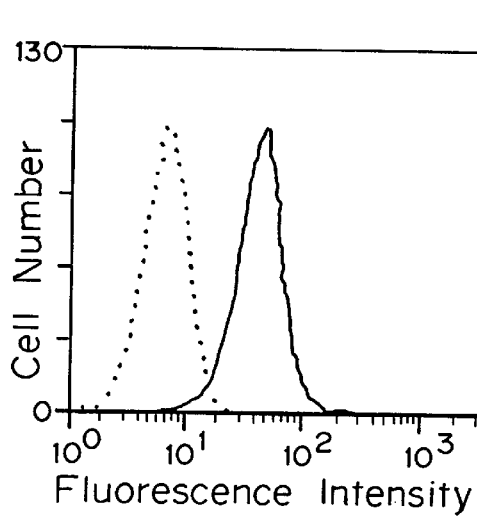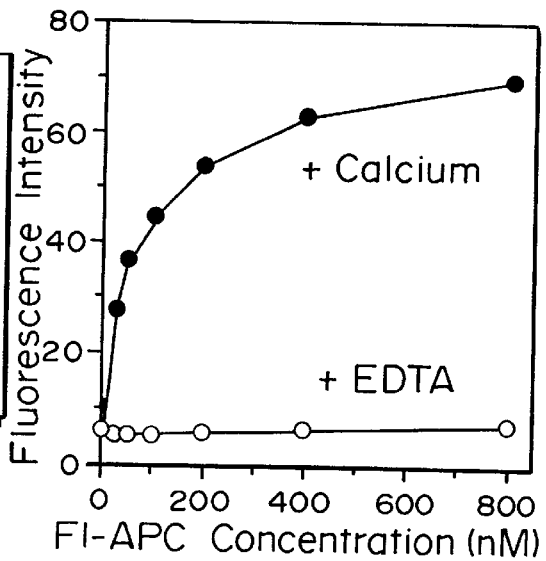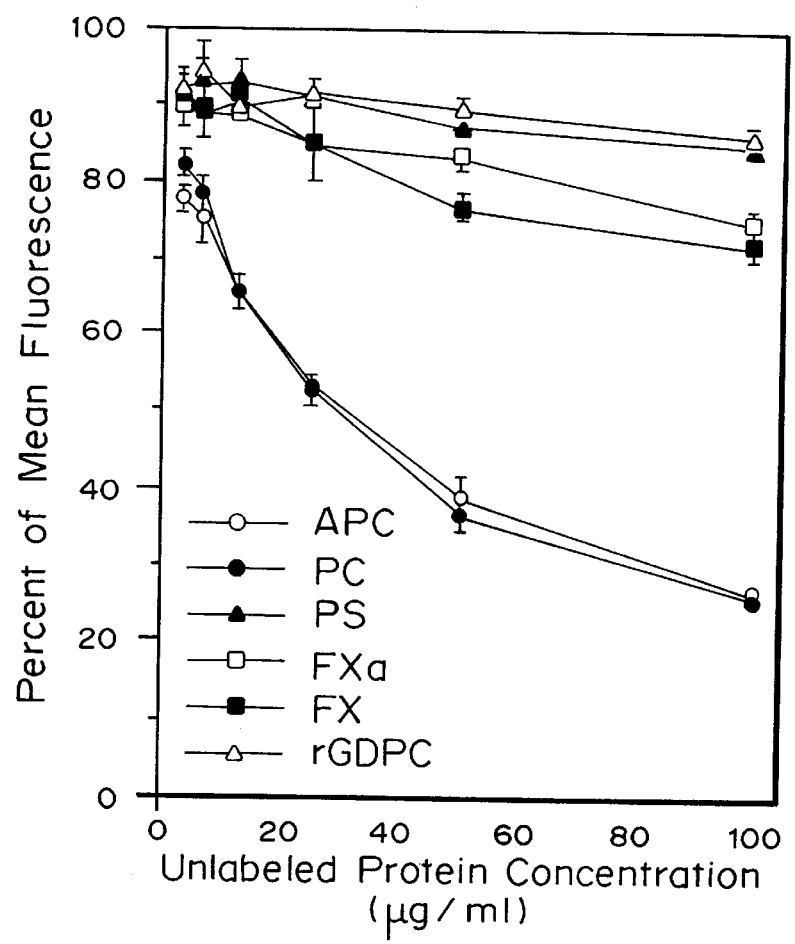
FIG. 1a
FIG. 1b
FIG. 1c

FIG. 4a

```
CAGGTCCGGAGCCTCAACTTCAGGATGTTGACAACATTGCTGCCGATACTGCTGCTGTCT  60
                    M  L  T  T  L  L  P  I  L  L  L  S         12

GGCTGGGCCTTTTGTAGCCAAGACGCCTCAGATGGCCTCCAAAGACTTCATATGTCCAG  120
 G  W  A  F Ⓒ S  Q  D  A  S  D  G  L  Q  R  L  H  M  L  Q    32

ATCTCCTACTTCCGGGACCCTATCACGTGTGTGGTACCAGGGCAACGCG TCGCTGGGGGGA 180
 I  S  Y  F  R  D  P  Y  H  V  W  Y  Q  G  |N  A  S| L  G  G    52

CACCTAACGCACGTGCTGGAAGGCCCAGACACCAACACCACGATCATTCAGCTGCAGCCC 240
 H  L  T  H  V  L  E  G  P  D  T |N  T  T| I  I  Q  L  Q  P    72

TTGCAGGAGCCCGAGAGCTGGGCGCGAGTGGCCGAGTCCAGTCCTACTGTCCAG 300
 L  Q  E  P  E  S  W  A  R  T  Q  S  G  L  Q  S  Y  L  L  Q    92

TTCCACGGGCTCGTGCGCCTGGTGCACCAGGAGCGGACCTTGGCCTTTCCTCTGACCATC 360
 F  H  G  L  V  R  L  V  H  Q  E  R  T  L  A  F  P  L  T  I   112

CGCTGCTTCCTGGGCTGTGAGCTGCCTCCCGAGGCTCTAGAGCCCATGTCTTCTTCGAA 420
 R Ⓒ F  L  G Ⓒ E  L  P  P  E  G  G  S  R  A  H  V  F  F  E   132
```

FIG. 4b

```
GTGGCTGTGAATGGGAGCTCCTTTGTGAGTTTCCGGCCGGAGAGAGCCTTGTGGCAGGCA      480
 V  A  V  N  G  S  S  F  V  S  F  R  P  P  E  R  A  L  W  Q  A    152

GACACCCAGGTCACCTCCGGAGTGGTCACCTTCACCCTGCAGCAGCTCAATGCCTACAAC      540
 D  T  Q  V  T  S  G  V  V  T  F  T  L  Q  Q  L  N  A  Y  N       172

CGCACTCGGTATGAACTGCGGGAATTCCTGGAGGACACCTGTGTGCAGTATGTGCAGAAA      600
 R  T  R  Y  E  L  R  E  F  L  E  D  T  C  V  Q  Y  V  Q  K       192

CATATTTCCGCGGAAAACACGAAAGGGAGCCAAACAAGCCGTTCATCATTGCTGGTGGTC      660
 H  I  S  A  E  N  T  K  G  S  Q  T  S  R  S  Y  T  S  L  V       212

CTGGGCGTCCTGGTGGGGCGGTTCATCATTGCTGGTGTGGCTGTAGGCATCTTCCTGTGC      720
 L  G  V  L  V  G  G  F  I  I  A  G  V  A  V  G  I  F  L  C       232

ACAGGTGGACGGGCGATGTTAATTACTCTCCAGCCCCGTCAGAAGGGGCTGGATTGATGGA      780
 T  G  G  R  R  C  *  238
```

FIG. 4C

```
GGCTGGCAAGGGAAAGTTTCAGCTCACTGTGAAGCCAGACTCCCAACTGAAACACCAGA    840
AGGTTTGGAGTGACAGCTCCTTCTCTCCCACATCTGCCCACTGAAGATTTGAGGGAGG     900
GGAGATGGAGAGGAGGTGGACAAAGTACTGGTTTGCTAAGAACCTAAGAACGTGTAT      960
GCTTTGCTGAATTAGTCTGATAAGTGAATGTTTATCTTTGTGAAAACAGATAATG       1020
GAGTTGGGGCAGGAAGCCTATGCGCCATCCTCCAAAGACAGAATCACCTGAGGCGT      1080
TCAAAAGATATAACCAAATAAACAAGTCATCCACAAATACAACATTCAATACTTC       1140
CAGGTGTGTCAGACTTGGGATGGGACGCTGATATAATAGGGTAGAAAGAAGTAACACGAA  1200
GAAGTGGTGGAAATGTAAATCCAAGTCATATGGCAGTGATCAATTATTAATCAATTAAT   1260
AATATTAATAAATTCTTATATTTAAAAAAAAAAAAAAAAAA                     1302
```

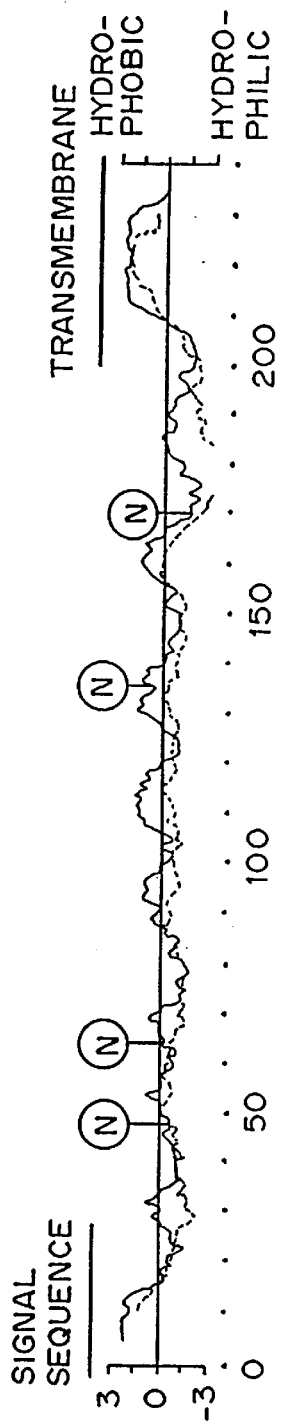

FIG. 5a

```
EPCR   MLTT..LLPILLLSGWAFCSQDASDGLQRLHMLQISYFRDPYHVWYQGNASLGGHLTHVL
CCD41  MLTKFLLLLLLLLLPGCAFVTPMAPKAAYAPDLL.....FPRPPSCEASGQRSLGKLLTHTL
CD1d   MGC...LLFLLLLWALLQAWGSAEVPQRLFPLRCLQISSFANSSWTRTDGLAWLGELQTHSW
MCD1.2 MRY..LPCLLLWAFLQVWGQSEVQQKNYTFRCLQTSSFANISWSRTDSLILLGDLQTHRW

EPCR   EGPDTNTTIIQLQPLQEPESWARTQSGLQSYLLQFHGLVRLVHQER......TLAFPLTI
CCD41  EGPSQNVTILQLQPWQDPESWERTESGLQIYLTQFESLVKLVYRER....KENVFFPLTV
CD1d   SN..DSDTVRSLRKPWSQGTFSDQQWETLQHIFRVYRSSFTRDVKEFAKML..RLSYPLEL
MCD1.2 SN..DSAITISFTKPWSQGKLSNQQWEKLQHMFQVYRVSFTRDIQELVKMMSPKEDYPIEI

EPCR   RCFLGCEL.P...PEGSRAHVFFEVAVNGSSFVSFRPERALWQADTQVTSGVTFTLQQL
CCD41  SCSLGCEL..PEEEEGSEPHVFFDVAVNGSAFVSFRPKTAVMWVSGSQEPSKAANFTLKQL
CD1d   QVSAGCEVHP.....GNASNNFFHVAFQGKDILSFQGTS..WEP.TQEAPLWVNLAIQVL
MCD1.2 QLSTGCEMYP.....GNASESFHVAFQGKYAVRFRGTS..WQR.VLGAPSWLDLPIKVL
```

FIG. 5b

```
        *      **   *  ***  ***            *        **     **          *   *
EPCR    ..........NAYNRTRYELREFLEDTCVQYV.........QKHISAENTKGSQTS..........................
CCD41   ..........NAYNRTRYELQEFLQDTCVEFL.........ENHITTQNMKGSQTG..........................
CD1d    ..........NQDKWTRETVQWLLNGTCPQFVSGLLESGKSELKKQVKPKAWLSRGPSPGPGRLLLVCHVSG
MCD1.2  ..........NADQGTSATVQTLLNDTWPQFARGLLEAGKSDLEKQEKPVAWLSSVPSSAHGHLQLVCHVSG

EPCR    ..................................................................
CCD41   ..................................................................
CD1d    FYPKPVWVKWMRGEQEQQGTQPGDILPNADETWYLRATLDVVAGEAAGLSCRVKHSSLEG
MCD1.2  FYPKPVWVMWMRGDQEQQGTHRGDFLPNADETWYLQATLDVEAGEEAGLACRVKHSSLGG

****  *  ***         *                        **
EPCR    .........RSYTSLVLGVLVGGFIIAGVAVGIFLCTGGRRC
CCD41   .........RSYTSLVLGILMGCFIIAGVAVGIFMCTSGRGLLII
CD1d    QDIVLYWGGSYTSMGLIALAVLACLLFLLIVGFTS.RFKRQTSYQGVL
MCD1.2  QDIILYWDARQAPVGLIVFIVLIMLVVGAVVYYI.WRRRSAYQDIR
```

```
  1 MLTTLLP..ILLLSGWAFCSQDASDGLQRLHMLQISYFRDPYHVWYQGNA 48
    ||·||  ·|||·||·|· |||·|| ||||||||·|··||·||||
  1 MLTKFLPLLLLLLPGCALCN...SDGSQSLHMLQISYFQDHHHVRHQGNA 47

49 SLGGHLTHVLEGPDTNTTIIQLQPLQEPESWARTQSGLQSYLLQFHGLVR 98
    |||  |||·||||·|·||·||||·|·|||·||·||||  ||·  ·||·
 48 SLGKLLTHTLEGPSQNVTILQLQPWQDPESWERTESGLQIYLTQFESLVK 97

99 LVHQER..TLAFPLTIRCFLGCELP...PEGSRAHVFFEVAVNGSSFVSF 143
    ||·||   ·||||·| ||||||    ·|||·||||·||||  ||·||||
 98 LVYRERKENVFFPLTVSCSLGCELPEEEEEGSEPHVFFDVAVNGSAFVSF 147

144 RPERALWQADTQVTSGVVTFTLQQLNAYNRTRYELREFLEDTCVQYVQKH 193
    ||·|·|··| ·| ···|||·||||||||||||||·|||·||||····|
148 RPKTAVWVSGSQEPSKAANFTLKQLNAYNRTRYELQEFLQDTCVEFLENH 197

194 ISAENTKGSQTSRSYTSLVLGVLVGGFIIAGVAVGIFLCTGGRRC 238
    |···| ||||·|||||||||·|·|· |||||||||||·||·||||
198 ITTQNMKGSQTGRSYTSLVLGILMGCFIIAGVAVGIFMCTSGRRC 242
```

FIG. 6

CLONING AND REGULATION OF AN ENDOTHELIAL CELL PROTEIN C/ACTIVATED PROTEIN C RECEPTOR

This is a divisional of U.S. Ser. No. 08/289,699, filed on Aug. 12, 1994, now U.S. Pat. No. 5,695,993.

BACKGROUND OF THE INVENTION

The present invention is generally in the area of cloning, expression, and regulation of an endothelial cell protein C/activated protein C receptor.

Protein C plays a major role in the regulation of blood coagulation. Patients deficient in protein C usually exhibit life threatening thrombotic-complications in infancy (Seligsohn et al., (1984) *N. Engl. J. Med.* 310, 559–562; Esmon, (1992) *Trends Cardiovasc. Med.* 2, 214–220) that are corrected by protein C administration (Dreyfus et al., (1991) *N. Engl. J. Med.* 325, 1565–1568). In addition, activated protein C (APC) can prevent the lethal effects of *E. coli* in baboon models of gram negative sepsis (Taylor et al., (1987) *J. Clin. Invest.* 79; U.S. Pat. No. 5,009,889 to Taylor and Esmon) and preliminary clinical results suggest that protein C is effective in treating certain forms of human septic shock (Gerson et al., (1993) *Pediatrics* 91, 418–422). These results suggest that protein C may both control coagulation and influence inflammation. Indeed, inhibition of protein S, an important component of the protein C pathway, exacerbates the response of primates to sublethal levels of *E. coli* and augments the appearance of TNF in the circulation (Taylor et al., (1991) *Blood* 78, 357–363). The mechanisms involved in controlling the inflammatory response remain unknown.

Protein C is activated when thrombin, the terminal enzyme of the coagulation system, binds to an endothelial cell surface protein, thrombomodulin (Esmon, (1989) *J. Biol. Chem.* 264, 4743–4746; Dittman and Majerus, (1990) *Blood* 75, 329–336; Dittman, (1991) *Trends Cardiovasc. Med.* 1, 331–336). In cell culture, thrombomodulin transcription is blocked by exposure of endothelial cells to tumor necrosis factor (TNF) (Conway and Rosenberg, (1988) *Mol. Cell. Biol.* 8, 5588–5592) and thrombomodulin activity and antigen are subsequently internalized and degraded (Lentz et al., (1991) *Blood* 77, 543–550, Moore, K. L., et. al., (1989) *Blood* 73, 159–165). In addition, C4bBP, a regulatory protein of the complement system, binds protein S to form a complex that is functionally inactive in supporting APC anticoagulant activity in vitro (Dahlback, (1986) *J. Biol. Chem.* 261, 12022–12027) and in vivo (Taylor, et al., 1991). Furthermore, C4bBP behaves as an acute phase reactant (Dahlback, (1991) *Thromb. Haemostas.* 66, 49–61). Thus, proteins of this pathway not only appear to regulate inflammation, but they also interact with components that regulate inflammation, and they themselves are subject to down regulation by inflammatory mediators.

Given the central role of the protein C pathway in regulating the host response to inflammation and the critical role of the pathway in controlling blood coagulation, it is important to identify and characterize all of the components that interact with the system. This is especially true since the molecular basis of the anti-inflammatory effects of the protein C pathway components have yet to be elucidated at the molecular level.

It is therefore an object of the present invention to provide a cellular receptor for protein C and activated protein C.

It is a further object of the present invention to provide nucleotide sequences encoding the cellular receptor and amino acid characterization of the receptor which allows expression of recombinant native and modified forms of the receptor.

It is another object of the present invention to provide methods of modulating the inflammatory response involving protein C and activated protein C.

SUMMARY OF THE INVENTION

An endothelial cell protein C binding protein (referred to herein as "EPCR") has been cloned and characterized. The protein is predicted to consist of 238 amino acids, which includes a 15 amino acid signal sequence at the N-terminus, and a 23 amino acid transmembrane region which characterizes the receptor as a type 1 transmembrane protein. The protein binds with high affinity to both protein C and activated protein C (Kd=30 nM) and is calcium dependent. The message and binding function of the receptor are both down regulated by cytokines such as TNF.

These results identify a new member of a complex pathway that, like other members of the pathway, is subject to regulation by inflammatory cytokines, and can therefore be used to modulate inflammatory reactions in which protein C or activated protein C is involved. Inhibition of the inflammatory response can be obtained by infusing soluble EPCR. Alternatively, localizing EPCR to surfaces in contact with blood will render the surfaces anticoagulant by virtue of the ability of EPCR to bind and concentrate the anticoagulant activated protein C at the surface. Alternatively, the function of EPCR can be enhanced by overexpressing the EPCR in endothelium that could be used to coat vascular grafts in patients with vascular disease or on stents in cardiac patients.

BRIEF DESCRIPTION OF THE DRAWINGS

FIGS. 1A, 1B and 1C are flow cytometric analyses of F1-APC (fluorescent labelled activated protein C) binding to HUVEC (human umbilical vein endothelial cells). FIG. 1A is a graph of cell number versus log of fluorescence intensity, demonstrating F1-APC binding to HUVEC. HUVEC ($1 \times 10^5$) were incubated at room temperature without (dotted line) or with 160 nM of F1-APC (solid line) in the presence of 1.3 mM $CaCl_2$. After washing, bound APC was analyzed by flow cytometry. FIG. 1B is a graph of fluorescence intensity versus F1-APC concentration (nM) demonstrating the concentration dependence of F1-APC binding to HUVEC. HUVEC were incubated with F1-APC in the absence (open circles) or presence of 1.3 mM $CaCl_2$ (closed circles) and binding was measured as in A. Mean channel fluorescence intensity is plotted for each F1-APC concentration (between 0 and 800 nM). FIG. 1C is a graph of the percent of mean fluorescence versus unlabeled protein concentration ($\mu g/ml$), demonstrating the effects of unlabeled proteins on F1-APC binding to HUVEC. F1-APC binding to HUVEC was carried out in the presence of the indicated concentrations (between 0 and 100 $\mu g/ml$) of unlabeled APC, protein C, protein S, factor X and Xa or recombinant Gla-domainless protein C (rGDPC).

FIG. 2A is a graph of the bound APC ($cpm \times 10^{-3}$) versus time (min), showing the time course of $^{125}$I-APC binding to HUVEC. HUVEC monolayers ($1.2 \times 10^5$ cells) were incubated at 4° C. with 32 nM (filled squares) or 8 nM (open squares) $^{125}$I-APC. At the indicated times, cells were washed and bound radioactivity was measured. FIG. 2B is a graph of bound APC ($cpm \times 10^{-3}$) versus unlabeled protein (nM) demonstrating the effects of unlabeled APC and rGDPC on $^{125}$I-APC binding to HUVEC. HUVEC were incubated at 4° C. for one hour with $^{125}$I-labeled APC in the presence of the indicated concentrations (between 01 and approximately 1000 nM) of unlabeled APC (open circles) or rGDPC (closed circles). After washing, bound radioactivity was measured. FIG. 2C is a graph of bound APC (fmol/well) versus free APC (nM) demonstrating the concentration dependence of $^{125}$I-APC binding to HUVEC. Monolayers of HUVEC were incubated with the concentrations of $^{125}$I-APC indicated as described above. Specific binding was determined as described below. FIG. 2D is a Scatchard analysis of $^{125}$I-APC binding to HUVEC. Each value was calculated from the data shown in FIG. 2C.

FIG. 4 is the predicted protein structure of EPCR based on nucleotide sequence, predicted amino acid sequence and a hydropathy plot of EPCR. The signal sequence and transmembrane region are indicated with the solid bars.

FIG. 5 is a comparison of the amino acid sequence of EPCR to the amino acid sequences of other members of the CD1 family and CCD41. The EPCR sequence is shown in the first line and compared to murine CCD41 (second line). human CD1d (third line) and murine CD1.2 (fourth line). Identities with EPCR are indicated by open boxes. Residues that are conserved between EPCR and all of the human CD1 family members are indicated by a double asterisk. Residues shared with one or more members of the CD1 family are indicated by a single asterisk.

FIG. 6 is a comparison of the amino acid sequence of human EPCR (first line) to the amino acid sequence of murine EPCR (second line). Identities are indicated by boxes. Similarities are indicated with an asterisk.

DETAILED DESCRIPTION OF THE INVENTION

Figure 2A:
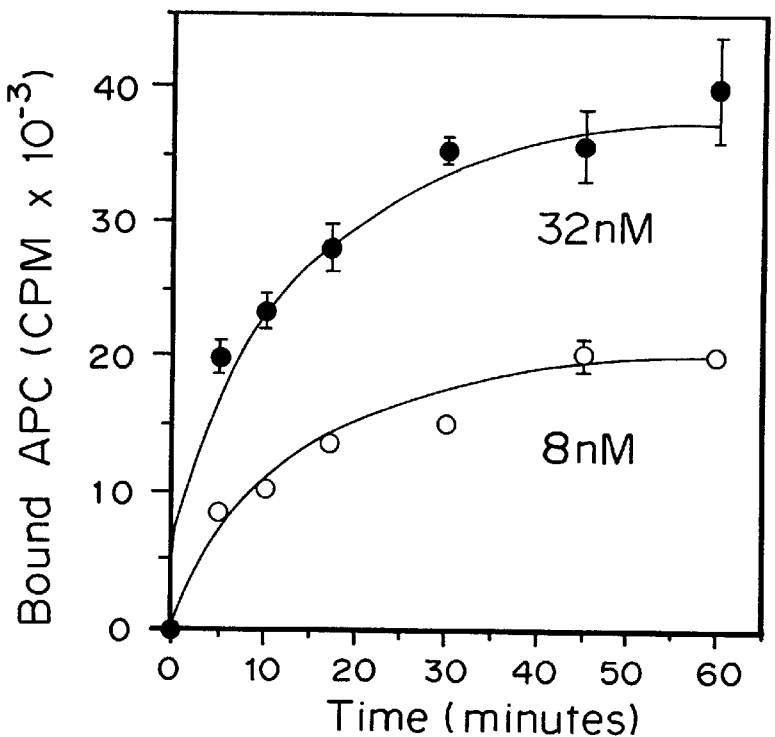
FIGS. 2A, 2B, 2C and 2D are graphs of $^{125}$I-APC Binding to HUVEC Monolayers.

I. Cloning and Characterization of EPCR.

Human protein C and activated protein C are shown to bind to endothelium specifically, selectively and saturably (Kd=30 nM, 7000 sites per cell) in a $Ca^{2+}$ dependent fashion. FL-APC binding to various human cell lines were examined, and found that the binding was HUVEC specific. A human kidney cell line transformed with SV40 large T antigen, 293T cells, expressed very few of these binding sites. A HUVEC cDNA library was constructed using the powerful mammalian expression vector, PEF-BOS (Mizushima and Nagata, (1990) *Nucleic Acids Res.* 18, 5322). Plasmid DNA was prepared from subpools of independent colonies (2,500 colonies per pool), and transfected into 293T cells, using the method of Kaisho et al., (1994) *Proc. Natl. Acad. Sci. (U.S.A.)* 91, 5325. FL-APC binding was analyzed on a flow cytometer. One of eight subpools gave a positive signal. This subpool was divided into 20 subpools and rescreened. After three rounds of enrichment, one positive clone, EPCR-1, was isolated. EPCR-1 carries a 1.3 kb insert. When transfected into 293T cells, this clone was capable of expressing the calcium-dependent binding site for FL-APC on the 293T cell surface.

Expression cloning revealed a 1.3 kb cDNA that coded for a type I transmembrane glycoprotein capable of binding protein C. This protein appears to be a member of the CD1/MHC superfamily. Like thrombomodulin, the receptor involved in protein C activation, the endothelial cell protein C receptor (EPCR) function and message are both down regulated by exposure of endothelium to TNF. Identification of EPCR as a member of the CD1/MHC superfamily provides insights into the role of this receptor for protein C in regulating the inflammatory response.

Materials and Methods

Protein Preparation

Human protein C (Esmon et al., (1993) *Meths. Enzymol.* 222, 359–385), APC (Esmon et al., 1993), recombinant gla domainless protein C (rGDPC) (Rezaie et al., (1992) *J. Biol. Chem.* 267, 11701–11704), protein S (Taylor et al., 1991), factor X and factor Xa (Le Bonniec et al., (1992) *J. Biol. Chem.* 267, 6970–6976) were prepared as described in the cited publications.

Selective labeling of the active site of APC with fluorescein was performed by the method of Bock (Bock, P. E. (1988) *Biochemistry* 27, 6633–6639). In brief, $N^\alpha$[(acetylthio)acetyl]-D-Phe-Pro-Arg-$CH_2$Cl (200 $\mu$M) was reacted with 40 $\mu$M APC for 1 hour at room temperature. After dialysis, the covalently modified APC was incubated at room temperature for one hour with 200 $\mu$M 5-(iodoacetamido)fluorescein (Molecular Probes). Free fluorescein was removed by gel filtration on a PD-10 column (Pharmacia). With this method, each molecule of fluoresceinated APC (Fl-APC) contains a single dye at the active site and hence all of the fluorescent molecules behave identically.

Iodogen (Pierce) was used to radiolabel APC with Na[$^{125}$I] (Amersham) according to the manufacture's protocol in the presence of 5 mM $CaCl_2$. Free $^{125}$I was removed by gel filtration on a PD-10 column. The specific activity of the $^{125}$I-APC was $1\times10^4$ cpm/ng protein.

Cell Culture

Human umbilical vein endothelial cells (HUVEC) were isolated from fresh umbilical-cords by collagenase treatment and cultured in medium 199 containing 15% fetal bovine serum, 10 $\mu$g/ml heparin, and 0.5% endothelial cell growth supplement prepared from bovine brain extract (Maciag at al., (1979) *Proc. Natl. Acad. Sci. (U.S.A.)* 76, 5674–5678). HOS (ATCC CRL 1543), HEp-2 (ATCC CCL 23) and 293 cells (ATCC CRL 1573) transformed with SV40 large T antigen (293T, a gift from Dr. Kenji Oritani) were maintained in Earl's MEM supplemented with 10% fetal bovine serum. The human lymphocyte cell lines, Jurkat, MOLT3 (ATCC CRL 1552), Jijoye (ATCC CCL 87), Raji (ATCC CCL 86), U-937 (ATCC CRL 1593), HL-60 (ATCC CCL 240), and HEL (ATCC TIB 180), were maintained in RPMI-1640 medium supplemented with 10% fetal bovine serum.

Flow Cytometric Analysis of Fl-APC Binding to Cells

Adherent cells were harvested by incubation at 37° C. for 5 min in phosphate buffered saline (PBS) containing 0.02% EDTA. Cells were washed twice with EDTA/PBS and then once with Hank's balanced salt solution (HBSS). They were resuspended in HBSS containing 1% bovine serum albumin (BSA) and 0.02% sodium azide (binding buffer). Cells ($1\times10^5$) were incubated at room temperature for 45 min with FL-APC in the dark. After washing, they were resuspended in the binding buffer containing 0.5 $\mu$g/ml of propidium iodide. Bound Fl-APC was analyzed on a flow cytometer, FACScan (Becton Dickinson). Living cells were gated on a dot plot display of forward-scatter (FSC) versus fluorescence-2 (FL2), and Fl-APC binding was detected on the fluorescence-1 (FL-1) channel. All experiments were performed in duplicate.

125I-APC binding to HUVEC

Monolayers of HUVEC in 24-well microplates (Costar) ($1\times10^5$ cells per well) were washed twice with EDTA/PBS and once with ice-cold HBSS. Cells were then incubated at 4° C. for one hour in the binding buffer with $^{125}$I-APC. After washing three times with ice-cold HBSS, cells were released with the EDTA buffer, and the bound radioactivity was measured in a gamma counter (Isodata 500). To determine non-specific, calcium-independent adsorption of radioactivity, the cells were washed with EDTA/PBS and residual radioactivity in the cell pellet was measured. Non-specific binding of radioactivity was consistently less than 5% of the specific binding. The data was analyzed using the Enzfitter program (Elsevier Biosoft, Cambridge, U.K.).

Construction of HUVEC CDNA Library

Poly-A RNA was isolated from HUVEC ($1\times10^8$ cells) using the FastTrack™ mRNA isolation kit (Invitrogen). CDNA was synthesized from 3 µg of poly-A RNA using a Librarian™ I kit (Invitrogen). A BstX I adaptor was ligated, double stranded CDNA was fractionated by agarose gel electrophoresis, and cDNA longer than 700 bp was ligated into a mammalian expression vector, PEF-BOS (Mizushima and Nagata, 1990; this vector was a kind gift from Dr. S. Nagata). The construct was transfected into *E. coli* DH10B by electroporation (Bio-Rad Gene Pulser™). The library-consisted of $8\times10^6$ independent colonies with an average size of 2.0 kb.

Expression Cloning and Sequence Analysis

Approximately $2\times10^4$ independent colonies were divided into eight subpools (each containing 2,500 independent colonies) and plasmid DNA was prepared from each subpool. Sub-confluent 293T cells in 24-well microplates were transfected with 1 µg of the DNA by the calcium/phosphate method (Graham and Van Der Eb, (1973) *Virology* 52, 456–467). After 20 hours, the medium was changed, and culture was continued for another 24 hours. The subpools were screened for F1-APC binding by FACS analysis as described above. The positive library pool was then divided into 20 new pools and rescreened. After three rounds of screening, 96 individual clones were tested and one positive clone was identified.

The insert (1.3 kb) was subcloned into pBluescript™ (Stratagene), and the nucleotide sequence was determined using a Sequenase™ version 2.0 DNA Sequencing kit (USB). Nucleotide and protein database search employed the BLAST™ (NCBI) and FASTA™ programs (GCG) with GenBank, EMBL, and SwissProt databases.

Northern Blot Analysis

Total RNAs (15 µg) from various cells were isolated, electrophoresed through formaldehyde agarose gels and transferred to a nylon membrane (Hybond-N™, Amersham). The 483 bp Xba I fragment from the 5' end of the EPCR cDNA was labeled by random priming according to the manufacturer's instructions (Multiprime™ DNA labeling system, Amersham) and used for hybridization.

Protein C and APC Binding to HUVEC

Endothelial cells in suspension bound FL-APC, as monitored by flow cytometry, and demonstrated in FIG. 1A. Binding was saturable and $Ca^{2+}$ dependent, as shown by FIG. 1B. Optimal binding required at least 1 mM $Ca^{2+}$. FL-APC was displaced from the cell surface by APC and protein C equivalently, as shown by FIG. 1C. The homologous Gla-domain containing proteins, protein S, factor X, and its active form, factor Xa, failed to displace bound F1-APC, suggesting that there is a specific binding site for APC on the endothelial cell surface. Protein C binding was dependent on the Gla domain, since recombinant gla-domainless protein C (rGDPC) failed to displace F1-APC.

Figure 2B:
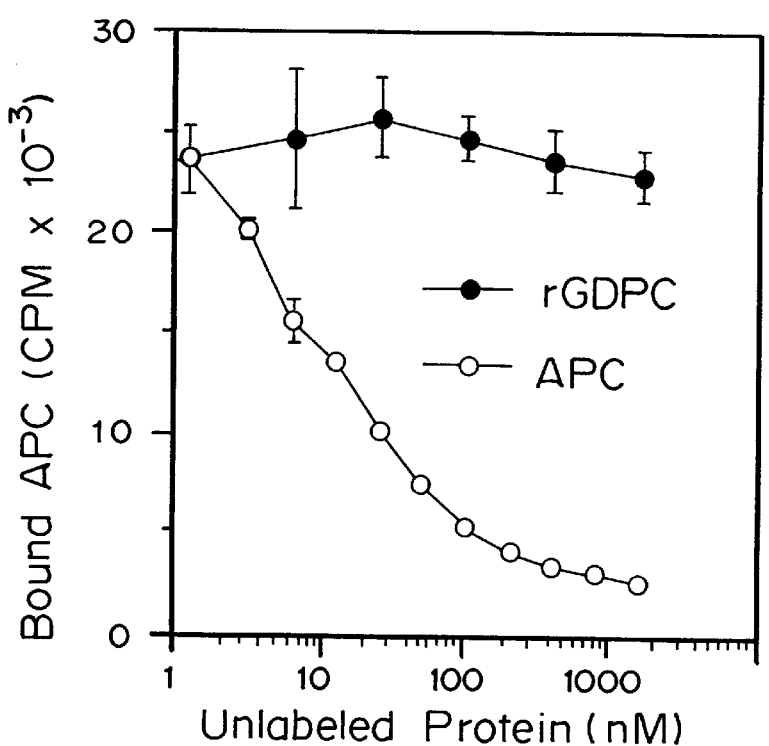
Figure 2C:
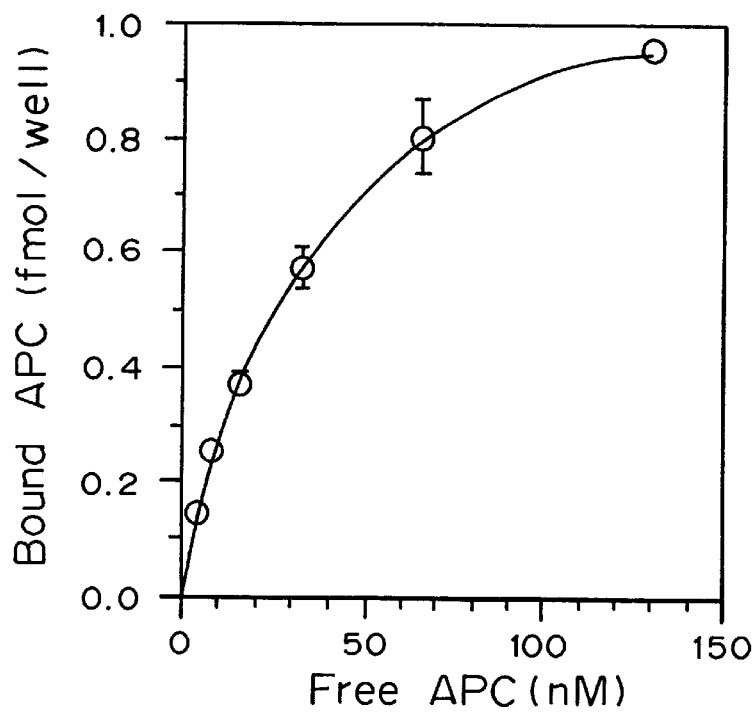
Figure 2D:
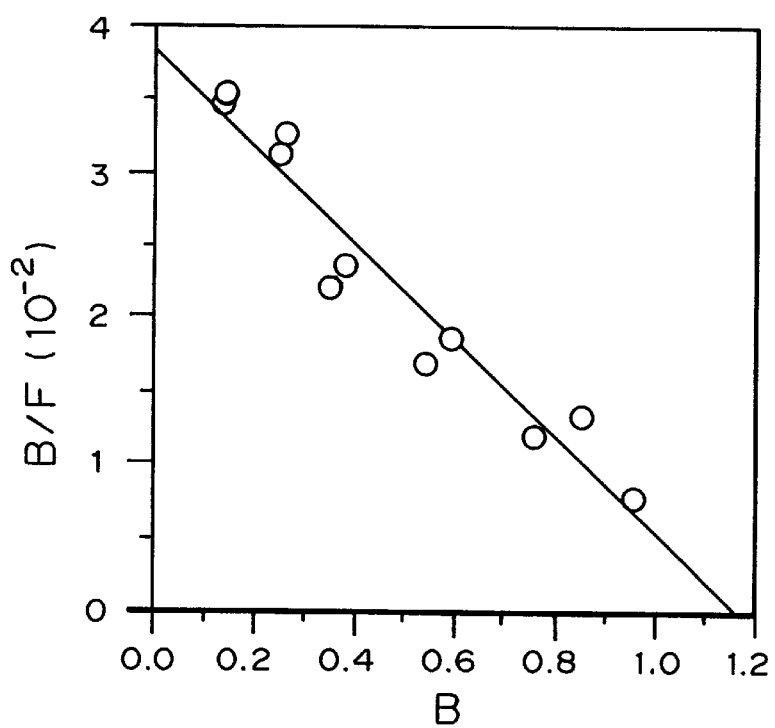
Figure 3A:
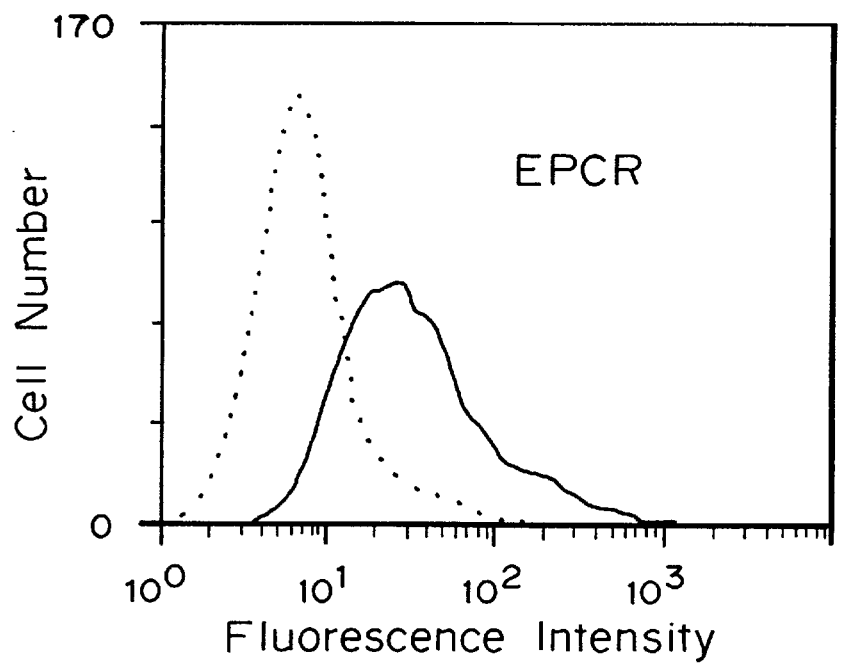
FIGS. 3A and 3B are flow cytometric analyses of Fl-APC binding to 293T cells transfected with a cDNA clone of EPCR. Cells were transfected with a clone EPCR/pEF-BOS or pEF-BOS (negative control) by the calcium/phosphate method. After 24 h, cells were harvested and Fl-APC binding was performed in the absence (dotted lines) or presence of 1.3 mM CaCl2 (solid lines).
Figure 3B:
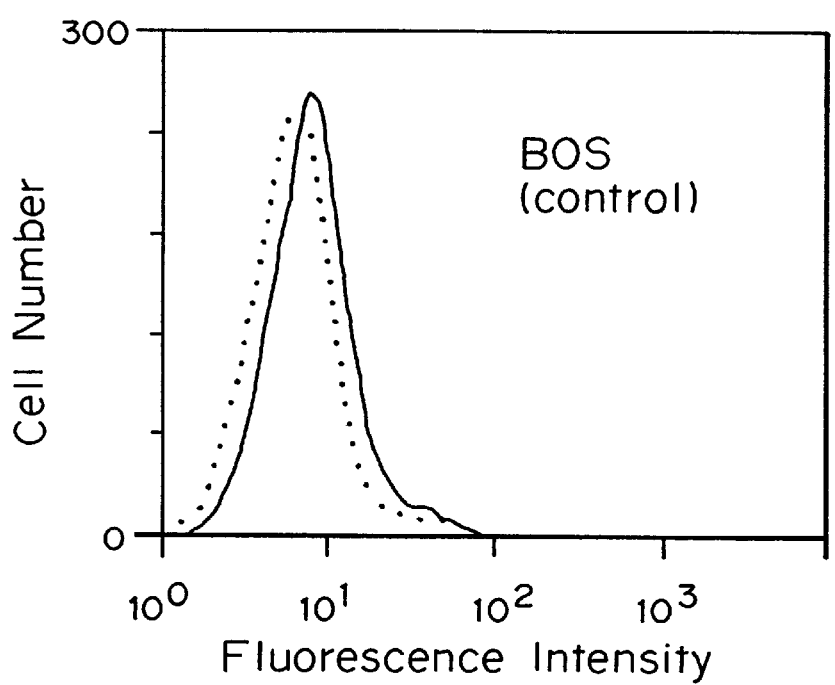

Detailed binding studies were also performed with $^{125}$I-labeled APC and monolayers of HUVEC, as shown by FIGS. 2A, 2B, 2C and 2D. The binding analysis indicated 7,000 sites per cell and a Kd=30 nM. This affinity is similar to that estimated from FIG. 1.

Endothelial cell surface thrombomodulin can interact with protein C and APC. The Kd (greater than 1 µM) (Hogg et al., (1992) *J. Biol. Chem.* 267, 703–706; Olsen et al., (1992) *Biochemistry* 31, 746–754), however, is much higher than that of the binding site described above with respect to the new receptor. Furthermore, polyclonal and monoclonal antibodies against thrombomodulin that inhibit protein C activation did not inhibit the binding. Protein S also can interact with protein C and APC (Dahlbäck et al., (1992) *Biochemistry* 31, 12769–12777), but F1-APC binding to HUVEC was not influenced by protein S addition. Furthermore, polyclonal and monoclonal antibodies to protein S did not inhibit the binding. These results indicate the binding site for protein C and APC on endothelium is distinct from these known molecules.

Nucleotide and Predicted Protein Structure Analysis of EPCR

The insert was subcloned into pBluescript, and the nucleotide sequence was determined, as shown in Sequence ID No. 1. The cDNA shown in Sequence ID No. 1 consists of 1302 bp, including a translation initiation ATG codon ( AGGATGT, (Kozak, (1986) *Cell* 44, 283–292) at the 5'-end at nucleotides 25–27 of Sequence ID No. 1. A potential polyadenylation signal sequence, AATAAA, (Proudfoot and Brownlee, (1976) *Nature* 263, 211–214) begins at nucleotide 1267 of Sequence ID No. 1, just 18 bp upstream of the poly(A) sequence.

The cDNA is predicted to code for a protein of 238 amino acids (Sequence ID No. 2), which includes a 15 amino acid signal sequence (von Heijne, (1986) *Nucleic Acids Res.* 14, 4683–4690) at the N-terminal. Therefore, the mature protein is predicted to contain 223 amino acids. Sequence ID No. 2 is the predicted amino acid sequence of EPCR. Amino acids 1–15 of Sequence ID No. 2 (MLTTLLPILLLSGWA) are the putative signal sequence determined by the method of von Heijne (von Heijne, 1986). Amino acids 211–236 of Sequence ID No. 2 (LVLGVLVGGFIIAGVAVGIFLCTGGR) are the putative transmembrane domain. Potential N-glycosylation sites are present at amino acids 47–49, 64–66, 136–138, and 172–174 of Sequence ID No. 2. Extracellular cysteine residues are present at amino acids 17, 114, 118, and 186 of Sequence ID No. 2. A potential transmembrane region (Engelman et al., (1986) *Annu. Rev. Biophys. Biophys. Chem.* 15, 321–53 ) consisting of 23 amino acids was identified at the C-terminal end (beginning at amino acid 211 of Sequence ID No. 2).

The protein is predicted to be a type 1 transmembrane protein. The extracellular domain contains four potential N-glycosylation sites and four Cys residues. The cytoplasmic region contains only three amino acids and terminates with a Cys, which could be acylated to something or involved in heterodimer formation with another peptide.

Although described with reference to cloning and expression of the protein encoding sequence, larger amounts of protein can be obtained by expression in suitable recombinant host systems, such as mammalian, yeast, bacteria, or insect cells. Isolation can be facilitated by making antibodies to the recombinant protein which are then immobilized on substrates for use in purification of additional receptors, as described below.

As used herein, the nucleotide sequences encoding the receptor include the sequence shown in Sequence ID No. 1, and sequences having conservative substitutions, additions or deletions thereof which hybridize to Sequence ID No. 1 under stringent conditions. As used herein, the amino acids sequences constituting the receptor include the sequence shown in Sequence ID No. 2, and sequences having conservative substitutions, additions or deletions thereof which form a receptor having functionally equivalent biological activity. It is well known to those skilled in the art what constitutes conservative substitutions, additions or deletions, and which could be readily ascertained as encoding, or forming, a functionally equivalent receptor molecule using the functional assays described herein.

The hydropathic plot shown in FIG. 4 was performed according to the method of Goldman et al (Engelman et al., 1994) (solid line) and that of Kyte and Doolittle (1982) $J. Mol. Biol.$ 157, 105–132 (dotted line).

DNA and protein database searches revealed that the sequence is related to the centrosome-associated, cell cycle dependent murine protein, CCD41, also referred as centrocyclin (Rothbarth et al., (1993) $J. Cell Sci.$ 104, 19–30), as shown by FIG. 5. The similarity in the published sequence of murine CCD41 with human EPCR led to the cloning and sequencing of the murine EPCR. The sequence of murine EPCR is shown in FIG. 6. It is distinct from the published sequence of CCD41.

The EPCR amino acid sequence was also related to, but quite distinct from, the CD1/MHC superfamily and the murine CD1.2, as also shown by FIG. 5. Based on the homology to CD1/MHC, it is likely that EPCR contains two domains consisting of residues 17–114 and 118–188. Of the CD1 family members, CD1d is the most similar to EPCR. In the mouse, CCD41 is associated exclusively with the centrosome during $G_1$ but becomes detectable elsewhere during the cell cycle, reaching a maximum during $G_2$, except during the $G_2$/M phase (Rothbarth et al., 1993). EPCR expression appears restricted to endothelium, which would not be expected for a cell cycle associated protein.

The identification of the protein C receptor on endothelium suggests that the endothelial cell binds protein C/APC through three distinct mechanisms. In addition to EPCR, protein S can bind APC/protein C on negatively charged membrane surfaces that include the endothelium (Stern et al., (1986) $J. Biol. Chem.$ 261, 713–718), but this is not cell type specific (Dahlback et al., 1992). Thrombomodulin in complex with thrombin can bind protein C and APC (Hogg et al., 1992). On endothelium, the protein S binding sites (Nawroth and Stern, (1986) $J. Exp. Med.$ 163, 740–745), thrombomodulin (Esmon, 1989) and EPCR are all down regulated by cytokines, indicating that inflammation can impair protein C pathway function at multiple levels.

The homology to the $CD^1$/MHC family of proteins is especially interesting since it provides indications as to the function of EPCR. The CD1/MHC family has three extracellular domains termed α1,2 and 3. The extracellular domain of EPCR contains four Cys residues that appear to correspond to two distinct domains. EPCR lacks the third domain of the CD1/MHC family, but the two domains have significant homology to the α1 and α2 domains of the CD1 protein family and the α2 domain of the MHC class 1 protein, suggesting that these proteins evolved from a common ancestor. The first domain of EPCR, residues 17–114, contains two potential N glycosylation sites and is rich in β strand structure, suggesting that it may form a β sheet. Despite the β strand structure, consensus sequences (Williams and Barclay, (1988) $Ann. Rev. Immunol.$ 6, 381–405) for the immunoglobulin superfamily of receptors are absent. The second domain of EPCR, residues 118–188, contains two additional N glycosylation sites and, like the CD1/MHC family, this domain is predicted to have limited β structure.

II. Modulation of Inflammation using EPCR.

In vitro studies have suggested anti-inflammatory activities for APC. For instance, an unusual carbohydrate sequence on protein C can inhibit inflammatory cell adhesion to selectins (Grinnell at al., (1994) $Glycobiology,$ 4, 221–226) Modest inhibitory effects of APC have been reported on TNF production (Grey et al., (1993) $Transplant. Proc.$ 25, 2913–2914). EPCR could contribute to these anti-inflammatory mechanisms. Since the homologous protein family, CD1, can be linked to CD8 (Ledbetter et al., (1985) $J. Immunol.$ 134, 4250–4254), it is also possible that the proteins C receptor is linked to another protein and signal through this second protein. One of the CD1 family members, CD1d, has been reported to promote T cell responses, possibly involving binding to CD8 (Panja et al., (1993) $J. Exp. Med.$ 178, 1115–1119). CD1b has recently been reported to serve as an antigen presenting molecule (Porcelli et al., (1992) $Nature$ 360, 593–597). The ability to bind protein C/APC could then be linked either directly or indirectly to signalling via direct interaction with cells of the immune system. Since the MHC class of proteins is involved in presentation of proteins to cell receptors, the concept of presentation of protein C/APC to inflammatory cells as a means of elaborating anti-inflammatory activity may also be involved. This includes modulation of enzyme specificity such as occurs with thrombin-thrombomodulin interaction (Esmon, 1989). In this case, the EPCR-APC complex might cleave biologically active peptides from unknown substrates.

EPCR mRNA Levels and APC Binding

To determine the cellular specificity of EPCR expression, the intensity of FL-APC binding to HUVEC was compared to several human cell lines. Fl-APC bound strongly only to HUVEC, and not to any of the T, B, or monocytic cell lines tested. Cells were incubated at room temperature without or with 160 nM F1-APC in the presence of 1.3 mM $CaCl_2$. Binding was analyzed by flow cytometry. Slight binding was demonstrated with the osteosarcoma line, HOS and the epidermoid carcinoma cell line, HEp-2.

Total RNA was extracted from these cells and hybridized with the EPCR cDNA probe for Northern Blot Analysis. EPCR mRNA was detected by Northern blot analysis for HUVEC, Jurkat, HEp-2, Raji, HOS, and U937. Among the cells lines tested, EPCR mRNA was detected at high levels only in HUVEC. The calculated mRNA size of 1.3 kb was identical to the size of the isolated cDNA. After prolonged exposure, a weak signal was also detected with the osteosarcoma cell line HOS and monocyte cell line U937. Thus, both APC binding and EPCR mRNA expression are very specific for endothelium.

Effects of TNF on APC Binding and EPCR MRNA Levels

Several other members of the protein C anticoagulant pathway are subject to regulation by inflammatory cytokines (Esmon, 1989). For instance, endothelial cell surface thrombomodulin expression and message are known to be reduced by exposure of the cells to TNF (Conway and Rosenberg, 1988; Lentz et al., 1991). To determine if a similar process occurs with EPCR, HUVEC were treated with TNF and APC binding and expression of EPCR mRNA were examined. APC binding to HUVEC decreased in a time dependent fashion. EPCR activity decreased more rapidly than thrombomodulin antigen. HUVEC were cultured for 0, 6, 24 and 48 hr, in the presence of TNF-α (10 ng/ml). Cells were harvested and residual F1-APC binding or thrombomodulin (TM) expression was analyzed by flow cytometry. Cell surface TM was stained with an anti-TM murine monoclonal antibody and FITC-conjugated anti-mouse IgG. The negative control is without added fluorescent ligand.

HUVEC were treated with 10 ng/ml of TNF-α for 0, 0.5, 1, 2, 3, 6, 10 and 24 hr, and message was extracted and detected as described above. The results demonstrated that the concentration of EPCR mRNA was also reduced by TNF treatment. Message levels and APC binding activity decreased in parallel. Therefore, the TNF mediated down-regulation of APC binding to endothelium probably occurs at the level of mRNA expression.

Enhancement of inflammatory responses by blocking binding of endogenous molecules to ECPCR can be achieved by administration of compounds binding to the receptor to a subject in need of inhibition. The degree of binding is routinely determined using assays such as those described above. Compounds which are effective include antibodies to the protein, fragments of antibodies retaining the binding regions, and peptide fragments of APC which include the Gla region. Inhibition of the inflammatory response could be obtained by infusing soluble EPCR. Alternatively, localizing EPCR to surfaces in contact with blood would render the surfaces anticoagulant by virtue of the ability of EPCR to bind and concentrate the anticoagulant APC at the surface. Alternatively, the function of EPCR could be enhanced by overexpressing the EPCR in endothelium used to coat vascular grafts in patients with vascular disease or on stents in cardiac patients.

The DNA sequence can also be used for screening for other homologous or structurally similar receptor proteins using hybridization probes.

These methods and reagents and pharmaceuticals are more readily understood by reference to the following.

Screening of patient samples for expression of receptor proteins.

Patients with thrombosis or hyperinflammatory conditions could be screened for defects in the EPCR gene. Sequence ID No. 1, and consecutive portions thereof of at least about seven nucleotides, more preferably fourteen to seventeen nucleotides, most preferably about twenty nucleotides, are useful in this screening using hybridization assays of patient samples, including blood and tissues. Screening can also be accomplished using antibodies, typically labelled with a fluorescent, radiolabelled, or enzymatic label, or by isolation of target cells and screening for binding activity, as described in the examples above. Typically, one would screen for expression on either a qualitative or quantitative basis, and for expression of functional receptor. Labelling can be with $^{32}P$, $^{35}S$, fluorescein, biotin, or other labels routinely used with methods known to those skilled in the art for labelling of proteins and/or nucleic acid sequences.

Hybridization Probes

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words, more stringent conditions. In general, the longer the sequence or higher the G and C content, the higher the temperature and/or salt concentration required. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Generation of Antibodies for Diagnostic or Therapeutic Use

Antibodies to the receptor proteins can also be generated which are useful in detection, characterization or isolation of receptor proteins, as well as for modifying receptor protein activity, in most cases, through inhibition of binding. Antibodies are generated by standard techniques, using human or animal receptor proteins. Since the proteins exhibit high evolutionary conservation, it may be advantageous to generate antibodies to a protein of a different species of origin than the species in which the antibodies are to be tested or utilized, looking for those antibodies which are immunoreactive with the most evolutionarily conserved regions. Antibodies are typically generated by immunization of an animal using an adjuvant such as Freund's adjuvant in combination with an immunogenic amount of the protein administered over a period of weeks in two to three week intervals, then isolated from the serum, or used to make hybridomas which express the antibodies in culture. Because the methods for immunizing animals yield antibody which is not of human origin, the antibodies could elicit an adverse effect if administered to humans. Methods for "humanizing" antibodies, or generating less immunogenic fragments of non-human antibodies, are well known. A humanized antibody is one in which only the antigen-recognized sites, or complementarily-determining hypervariable regions (CDRs) are of non-human origin, whereas all framework regions (FR) of variable domains are products of human genes. These "humanized" antibodies present a lesser xenographic rejection stimulus when introduced to a human recipient.

To accomplish humanization of a selected mouse monoclonal antibody, the CDR grafting method described by Daugherty, et al., (1991) *Nucl. Acids Res.,* 19:2471–2476, incorporated herein by reference, may be used. Briefly, the variable region DNA of a selected animal recombinant anti-idiotypic ScFv is sequenced by the method of Clackson, T., et al., (1991) *Nature,* 352:624–688, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The immunogenic stimulus presented by the monoclonal antibodies so produced may be further decreased by the use of Pharmacia's (Pharmacia LKB Biotechnology, Sweden) "Recombinant Phage Antibody System" (RPAS), which generates a single-chain Fv fragment (ScFv) which incorporates the complete antigen-binding domain of the antibody. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody. Compared to the intact monoclonal antibody, the recombinant ScFv includes a considerably lower number of epitopes, and thereby presents a much weaker immunogenic stimulus when injected into humans.

The antibodies can be formulated in standard pharmaceutical carriers for administration to patients in need thereof. These include saline, phosphate buffered saline, and other aqueous carriers, and liposomes, polymeric microspheres and other controlled release delivery devices, as are well known in the art. The antibodies can also be administered with adjuvant, such as muramyl dipeptide or other materials approved for use in humans (Freund's adjuvant can be used for administration of antibody to animals).

Screening for drugs modifying or altering the extent of receptor function or expression The receptor proteins are useful as targets for compounds which turn on, or off, or otherwise regulate binding to these receptors. The assays described above clearly provide routine methodology by which a compound can be tested for an inhibitory effect on binding of PC or APC. The in vitro studies of compounds which appear to inhibit binding selectively to the receptors are then confirmed by animal testing. Since the molecules are so highly evolutionarily conserved, it is possible to conduct studies in laboratory animals such as mice to predict the effects in humans.

In cases where inflammatory mediators or vascular disease down regulate EPCR, it would be advantageous to increase its concentration in vivo on endothelium. The binding assays described here and the gene sequence allow assays for increased EPCR expression. Similar approaches have been taken with thrombomodulin and investigators have shown that cyclic AMP (Maruyama, I. et al. (1991) *Thrombosis Research* 61, 301–310) and interleukin 4 (Kapiotis, S. et al., (1991) *Blood* 78, 410–415) can elevate thrombomodulin expression. The ability to screen such drugs or drugs that block TNF down regulation of EPCR provide an approach to elevating EPCR expression in vivo and thus enhancing anticoagulant and anti-inflammatory activity.

Studies based on inhibition of binding are predictive for indirect effects of alteration of receptor binding. For example, inhibition of binding of APC or increased expression of TNF is predictive of inhibition of EPCR function.

Assays for testing compounds for useful activity can be based solely on interaction with the receptor protein, preferably expressed on the surface of transfected cells such as those described above. Proteins in solution or immobilized on inert substrates can also be utilized. These can be used to detect inhibition or enhancement in binding of PC or APC Alternatively, the assays can be based on interaction with the gene sequence encoding the receptor protein, preferably the regulatory sequences directing expression of the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor activity in transfected or naturally occurring cells which express the receptor, then in vivo in laboratory animals. Typically, the antisense would inhibit expression. However, sequences which block those sequences which "turn off" synthesis can also be targeted.

The receptor protein for study can be isolated from either naturally occurring cells or cells which have been genetically engineered to express the receptor, as described in the examples above. In the preferred embodiment, the cells would have been engineered using the intact gene.

Random generation of receptor or receptor encoding sequence binding molecules.

Molecules with a given function, catalytic or ligand-binding, can be selected for from a complex mixture of random molecules in what has been referred to as "in vitro genetics" (Szostak, (1992) *TIBS* 19:89). One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer assisted drug design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., (1988) Acta Pharmaceutica Fennica 97, 159–166; Ripka, New Scientist 54–57 (Jun. 16, 1988); McKinaly and Rossmann, (1989) Annu. Rev. Pharmacol. Toxiciol. 29, 111–122; Perry and Davies, QSAR: quantitative Structure-Activity Relationships in Drug Design pp. 189–193 (Alan R. Liss, Inc. 1989); Lewis and Dean, (1989) Proc. R. Soc. Lond. 236, 125–140 and 141–162; and, with respect to a model receptor for nucleic acid components, Askew, et al., (1989) J. Am. Chem. Soc. 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Generation of nucleic acid regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, (1993) Science, 260, 926–932; U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., (1993) Science 261, 209–211; incorporated herein by reference).

The 5' flanking sequences of the receptor gene can also be used to inhibit the expression of the receptor. For example, an antisense RNA of all or a portion of the 5' flanking region of the receptor gene can be used to inhibit expression of the receptor in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the receptor gene can be inserted into an appropriate expression vector so that upon passage into the cell, the transcription of the inserted DNA yields an antisense RNA that is complementary to the mRNA transcript of the receptor protein gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the receptor protein gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., (1978) Proc. Natl. Acad. Sci. U.S.A. 75, 280–284; Zamecnik et al., (1986) Proc. Natl. Acad. Sci., 83, 4143–4146; Wickstrom et al., (1988) Proc. Natl. Acad. Sci. U.S.A. 85, 1028–1032; Crooke, (1993) FASEB J. 7, 533–539. Furthermore, recent work has shown that improved inhibition of expression of a gene by antisense oligonucleotides is possible if the antisense oligonucleotides contain modified nucleotides (see, e.g., Offensperger et. al., (1993) EMBO J. 12, 1257–1262 (in vivo inhibition of duck hepatitis B viral replication and gene expression by antisense phosphorothioate oligodeoxynucleotides); PCT WO 93/01286 Rosenberg et al., (synthesis of sulfurthioate oligonucleotides); Agrawal et al., (1988) Proc. Natl. Acad. Sci. U.S.A. 85, 7079–7083 (synthesis of antisense oligonucleoside phosphoramidates and phosphorothioates to inhibit replication of human immunodeficiency virus-1); Sarin et al., (1989) Proc. Natl. Acad. Sci. U.S.A. 85, 7448–7794 (synthesis of antisense methylphosphonate oligonucleotides); Shaw et al., (1991) Nucleic Acids Res 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., Maher et al., (1989) Science 245, 725–730; Orson et al., (1991) Nucl. Acids Res. 19, 3435–3441; Postal et al., (1991) Proc. Natl. Acad. Sci. U.S.A. 88, 8227–8231; Cooney et al., (1988) Science 241, 456–459; Young et al., (1991) Proc. Natl. Acad. Sci. U.S.A. 88, 10023–10026; Duval-Valentin et al., (1992) Proc. Natl. Acad. Sci. U.S.A. 89, 504–508; Blume et al., (1992) Nucl. Acids Res. 20, 1777–1784; Grigoriev et al., (1992) J. Biol. Chem. 267, 3389–3395.

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., (1988) Mol. Cell. Biol. 8, 963–973; Wickstrom et al., (1988) Proc. Natl. Acad. Sci. U.S.A. 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., (1984) *Ann. Rev. Biochem.* 53, 323–356 (phosphotriester and phosphite-triester methods); Narang et al., (1980) *Methods Enzymol.*, 65, 610–620 (phosphotriester method). Accordingly, DNA sequences of the 5' flanking region of the receptor protein gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a receptor protein gene in order to inhibit expression of the gene.

In some cases it may be advantageous to insert enhancers or multiple copies of the regulatory sequences into an expression system to facilitate screening of methods and reagents for manipulation of expression.

Preparation of Receptor Protein Fragments

Compounds which are effective for blocking binding of the receptor can also consist of fragments of the receptor proteins, expressed recombinantly and cleaved by enzymatic digest or expressed from a sequence encoding a peptide of less than the full length receptor protein. These will typically be soluble proteins, i.e., not including the transmembrane and cytoplasmic regions, although smaller portions determined in the assays described above to inhibit or compete for binding to the receptor proteins can also be utilized. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking receptor binding, the $IC_{50}$, the dose of peptide required to inhibit binding by 50%, ranges from about 1 μM to greater than 10 mM, depending on the peptide size and folding. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy.

As noted above, the peptides can be prepared by proteolytic cleavage of the receptor proteins, or, preferably, by synthetic means. These methods are known to those skilled in the art. An example is the solid phase synthesis described by J. Merrifield, (1964) *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 μg/kg of body weight. Based on extrapolation from other proteins, for treatment of most inflammatory disorders, the dosage range will be between 0.1 to 70 mg/kg of body weight. This dosage will be dependent, in part, on whether one or more peptides are administered.

Pharmaceutical Compositions

Compounds which alter receptor protein binding are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625, 214.

Disorders to be treated

As described herein, a variety of compounds can be used to inhibit or enhance expression of the EPCR. The nature of the disorder will determine if the expression should be enhanced or inhibited. For example, based on the studies involving the use of an anti-protein C antibody in combination with cytokine, it should be possible to treat solid tumors by enhancing an inflammatory response involving blocking of protein C or activated protein C binding to an endothelial cell protein C/activated protein C receptor by administering to a patient in need of treatment thereof an amount of a compound blocking binding of protein C or activated protein C to the receptor. Similarly, it should be possible to treat disorders such as gram negative sepsis, stroke, thrombosis, septic shock, adult respiratory distress syndrome, and pulmonary emboli using a method for inhibiting an inflammatory response involving administration of EPCR or EPCR fragments or substances that upregulate EPCR expression to a patient in need of treatment therof.

Modifications and variations of the methods and materials described herein will be obvious to those skilled in the art and are intended to be encompassed by the following claims. The teachings of the references cited herein are specifically incorporated herein.

We claim:

1. An isolated endothelial cell protein C/activated protein C receptor having the amino acid sequence of Sequence ID No. 2 or a sequence having conservative substitutions, additions or deletions thereof, having functionally equivalent receptor binding activity to activated Protein C.

2. The receptor of claim 1 having the amino acid sequence of Sequence ID No. 2.

3. The receptor of claim 1 expressed on the surface of a non-human cell or a non-endothelial cell.

4. The receptor of claim 1 lacking at least a portion of the transmembrane region.

5. The receptor of claim 4 in soluble form.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1302 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 1..1302
        ( D ) OTHER INFORMATION: /note= "Nucleotides 25 through 738
            encode the Endothelial Cell Protein Receptor of
            Sequence ID No. 2."

( x i ) SEQUENCE DESCRIPTION: SEQ ID NO:1:

```
CAGGTCCGGA  GCCTCAACTT  CAGGATGTTG  ACAACATTGC  TGCCGATACT  GCTGCTGTCT    60
GGCTGGGCCT  TTTGTAGCCA  AGACGCCTCA  GATGGCCTCC  AAAGACTTCA  TATGCTCCAG   120
ATCTCCTACT  TCCGCGACCC  CTATCACGTG  TGGTACCAGG  GCAACGCGTC  GCTGGGGGGA   180
CACCTAACGC  ACGTGCTGGA  AGGCCCAGAC  ACCAACACCA  CGATCATTCA  GCTGCAGCCC   240
TTGCAGGAGC  CCGAGAGCTG  GGCGCGCACG  CAGAGTGGCC  TGCAGTCCTA  CCTGCTCCAG   300
TTCCACGGCC  TCGTGCGCCT  GGTGCACCAG  GAGCGGACCT  TGGCCTTTCC  TCTGACCATC   360
CGCTGCTTCC  TGGGCTGTGA  GCTGCCTCCC  GAGGGCTCTA  GAGCCCATGT  CTTCTTCGAA   420
GTGGCTGTGA  ATGGAGCTC   CTTTGTGAGT  TTCCGGCCGG  AGAGAGCCTT  GTGGCAGGCA   480
GACACCCAGG  TCACCTCCGG  AGTGGTCACC  TTCACCCTGC  AGCAGCTCAA  TGCCTACAAC   540
CGCACTCGGT  ATGAACTGCG  GGAATTCCTG  GAGGACACCT  GTGTGCAGTA  TGTGCAGAAA   600
CATATTTCCG  CGGAAAACAC  GAAAGGGAGC  CAAACAAGCC  GCTCCTACAC  TTCGCTGGTC   660
CTGGGCGTCC  TGGTGGGCGG  TTTCATCATT  GCTGGTGTGG  CTGTAGGCAT  CTTCCTGTGC   720
ACAGGTGGAC  GGCGATGTTA  ATTACTCTCC  AGCCCCGTCA  GAAGGGGCTG  GATTGATGGA   780
GGCTGGCAAG  GGAAAGTTTC  AGCTCACTGT  GAAGCCAGAC  TCCCCAACTG  AAACACCAGA   840
AGGTTTGGAG  TGACAGCTCC  TTTCTTCTCC  CACATCTGCC  CACTGAAGAT  TGAGGGAGG   900
GGAGATGGAG  AGGAGAGGTG  GACAAAGTAC  TTGGTTTGCT  AAGAACCTAA  GAACGTGTAT   960
GCTTTGCTGA  ATTAGTCTGA  TAAGTGAATG  TTTATCTATC  TTTGTGGAAA  ACAGATAATG  1020
```

| | | | | | | |
|---|---|---|---|---|---|---|
| GAGTTGGGGC | AGGAAGCCTA | TGCGCCATCC | TCCAAAGACA | GACAGAATCA | CCTGAGGCGT | 1080 |
| TCAAAAGATA | TAACCAAATA | AACAAGTCAT | CCACAATCAA | AATACAACAT | TCAATACTTC | 1140 |
| CAGGTGTGTC | AGACTTGGGA | TGGGACGCTG | ATATAATAGG | GTAGAAAGAA | GTAACACGAA | 1200 |
| GAAGTGGTGG | AAATGTAAAA | TCCAAGTCAT | ATGGCAGTGA | TCAATTATTA | ATCAATTAAT | 1260 |
| AATATTAATA | AATTTCTTAT | ATTTAAAAAA | AAAAAAAAA | AA | | 1302 |

( 2 ) INFORMATION FOR SEQ ID NO:2:

( i ) SEQUENCE CHARACTERISTICS:
        ( A ) LENGTH: 238 amino acids
        ( B ) TYPE: amino acid
        ( D ) TOPOLOGY: linear ( i i ) MOLECULE TYPE: protein ( i i i ) HYPOTHETICAL: NO ( i x ) FEATURE:
        ( A ) NAME/KEY: misc_feature
        ( B ) LOCATION: 1..365
        ( D ) OTHER INFORMATION: /note= "Endothelial Cell Protein
        Receptor encoded by nucleotides 1 through 1302 of
        Sequence ID No. 1."

( i x ) FEATURE:
        ( A ) NAME/KEY: Modified-site
        ( B ) LOCATION: 1..15
        ( D ) OTHER INFORMATION: /note= "Amino acids 1-15 represent
        a putative signal sequence."

( i x ) FEATURE:
        ( A ) NAME/KEY: Domain
        ( B ) LOCATION: 211..236
        ( D ) OTHER INFORMATION: /note= "Amino acids 211-236
        represent a putative transmembrane domain."

( i x ) FEATURE:
        ( A ) NAME/KEY: Active-site
        ( B ) LOCATION: 47..174
        ( D ) OTHER INFORMATION: /note= "Amino acids 47-49, 64-66,
        136-138 and 172-174 represent potential
        N- glycosylation sites."

( i x ) FEATURE:
        ( A ) NAME/KEY: Modified-site
        ( B ) LOCATION: 17..186
        ( D ) OTHER INFORMATION: /note= "Amino acids 17, 114, 118
        and 186 represent extracellular cysteine
        residues."

( x i ) SEQUENCE DESCRIPTION: SEQ ID NO:2:

| Met | Leu | Thr | Thr | Leu | Leu | Pro | Ile | Leu | Leu | Leu | Ser | Gly | Trp | Ala | Phe |
|---|---|---|---|---|---|---|---|---|---|---|---|---|---|---|---|
| 1 | | | | 5 | | | | | 10 | | | | | 15 | |
| Cys | Ser | Gln | Asp | Ala | Ser | Asp | Gly | Leu | Gln | Arg | Leu | His | Met | Leu | Gln |
| | | | 20 | | | | | 25 | | | | | 30 | | |
| Ile | Ser | Tyr | Phe | Arg | Asp | Pro | Tyr | His | Val | Trp | Tyr | Gln | Gly | Asn | Ala |
| | | | 35 | | | | | 40 | | | | | 45 | | |
| Ser | Leu | Gly | Gly | His | Leu | Thr | His | Val | Leu | Glu | Gly | Pro | Asp | Thr | Asn |
| | | 50 | | | | | 55 | | | | | 60 | | | |
| Thr | Thr | Ile | Ile | Gln | Leu | Gln | Pro | Leu | Gln | Glu | Pro | Glu | Ser | Trp | Ala |
| 65 | | | | | 70 | | | | | 75 | | | | | 80 |
| Arg | Thr | Gln | Ser | Gly | Leu | Gln | Ser | Tyr | Leu | Leu | Gln | Phe | His | Gly | Leu |
| | | | | 85 | | | | | 90 | | | | | 95 | |
| Val | Arg | Leu | Val | His | Gln | Glu | Arg | Thr | Leu | Ala | Phe | Pro | Leu | Thr | Ile |
| | | | | 100 | | | | | 105 | | | | | 110 | |
| Arg | Cys | Phe | Leu | Gly | Cys | Glu | Leu | Pro | Pro | Glu | Gly | Ser | Arg | Ala | His |
| | | | 115 | | | | | 120 | | | | | 125 | | |

-continued

| Val | Phe | Phe | Glu | Val | Ala | Val | Asn | Gly | Ser | Ser | Phe | Val | Ser | Phe | Arg |
|---|---|---|---|---|---|---|---|---|---|---|---|---|---|---|---|
| | | 130 | | | | 135 | | | | | 140 | | | | |

| Pro | Glu | Arg | Ala | Leu | Trp | Gln | Ala | Asp | Thr | Gln | Val | Thr | Ser | Gly | Val |
|---|---|---|---|---|---|---|---|---|---|---|---|---|---|---|---|
| 145 | | | | | 150 | | | | | 155 | | | | | 160 |

| Val | Thr | Phe | Thr | Leu | Gln | Gln | Leu | Asn | Ala | Tyr | Asn | Arg | Thr | Arg | Tyr |
|---|---|---|---|---|---|---|---|---|---|---|---|---|---|---|---|
| | | | | 165 | | | | | 170 | | | | | 175 | |

| Glu | Leu | Arg | Glu | Phe | Leu | Glu | Asp | Thr | Cys | Val | Gln | Tyr | Val | Gln | Lys |
|---|---|---|---|---|---|---|---|---|---|---|---|---|---|---|---|
| | | | 180 | | | | | 185 | | | | | 190 | | |

| His | Ile | Ser | Ala | Glu | Asn | Thr | Lys | Gly | Ser | Gln | Thr | Ser | Arg | Ser | Tyr |
|---|---|---|---|---|---|---|---|---|---|---|---|---|---|---|---|
| | | 195 | | | | | 200 | | | | | 205 | | | |

| Thr | Ser | Leu | Val | Leu | Gly | Val | Leu | Val | Gly | Gly | Phe | Ile | Ile | Ala | Gly |
|---|---|---|---|---|---|---|---|---|---|---|---|---|---|---|---|
| | | 210 | | | | | 215 | | | | | 220 | | | |

| Val | Ala | Val | Gly | Ile | Phe | Leu | Cys | Thr | Gly | Gly | Arg | Arg | Cys | | |
|---|---|---|---|---|---|---|---|---|---|---|---|---|---|---|---|
| 225 | | | | | 230 | | | | | 235 | | | | | |

( 2 ) INFORMATION FOR SEQ ID NO:3:

( i ) SEQUENCE CHARACTERISTICS:
        ( A ) LENGTH: 244 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| Met | Leu | Thr | Lys | Phe | Leu | Leu | Leu | Leu | Leu | Leu | Leu | Leu | Pro | Gly | Cys |
|---|---|---|---|---|---|---|---|---|---|---|---|---|---|---|---|
| 1 | | | | 5 | | | | | 10 | | | | | 15 | |

| Ala | Phe | Val | Thr | Pro | Met | Ala | Pro | Lys | Ala | Ala | Tyr | Ala | Pro | Asp | Leu |
|---|---|---|---|---|---|---|---|---|---|---|---|---|---|---|---|
| | | | 20 | | | | | 25 | | | | | 30 | | |

| Leu | Phe | Pro | Arg | Pro | Pro | Ser | Cys | Glu | Ala | Ser | Gly | Gln | Arg | Ser | Leu |
|---|---|---|---|---|---|---|---|---|---|---|---|---|---|---|---|
| | | 35 | | | | | 40 | | | | | 45 | | | |

| Gly | Lys | Leu | Leu | Thr | His | Thr | Leu | Glu | Gly | Pro | Ser | Gln | Asn | Val | Thr |
|---|---|---|---|---|---|---|---|---|---|---|---|---|---|---|---|
| | 50 | | | | | 55 | | | | | 60 | | | | |

| Ile | Leu | Gln | Leu | Gln | Pro | Trp | Gln | Asp | Pro | Glu | Ser | Trp | Glu | Arg | Thr |
|---|---|---|---|---|---|---|---|---|---|---|---|---|---|---|---|
| 65 | | | | | 70 | | | | | 75 | | | | | 80 |

| Glu | Ser | Gly | Leu | Gln | Ile | Tyr | Leu | Thr | Gln | Phe | Glu | Ser | Leu | Val | Lys |
|---|---|---|---|---|---|---|---|---|---|---|---|---|---|---|---|
| | | | | 85 | | | | | 90 | | | | | 95 | |

| Leu | Val | Tyr | Arg | Glu | Arg | Lys | Glu | Asn | Val | Phe | Phe | Pro | Leu | Thr | Val |
|---|---|---|---|---|---|---|---|---|---|---|---|---|---|---|---|
| | | | 100 | | | | | 105 | | | | | 110 | | |

| Ser | Cys | Ser | Leu | Gly | Cys | Glu | Leu | Pro | Glu | Glu | Glu | Glu | Gly | Gly | Ser |
|---|---|---|---|---|---|---|---|---|---|---|---|---|---|---|---|
| | | | 115 | | | | | 120 | | | | | 125 | | |

| Glu | Pro | His | Val | Phe | Phe | Asp | Val | Ala | Val | Asn | Gly | Ser | Ala | Phe | Val |
|---|---|---|---|---|---|---|---|---|---|---|---|---|---|---|---|
| | | 130 | | | | | 135 | | | | | 140 | | | |

| Ser | Phe | Arg | Pro | Lys | Thr | Ala | Val | Trp | Val | Ser | Gly | Ser | Gln | Glu | Pro |
|---|---|---|---|---|---|---|---|---|---|---|---|---|---|---|---|
| 145 | | | | | 150 | | | | | 155 | | | | | 160 |

| Ser | Lys | Ala | Ala | Asn | Phe | Thr | Leu | Lys | Gln | Leu | Asn | Ala | Tyr | Asn | Arg |
|---|---|---|---|---|---|---|---|---|---|---|---|---|---|---|---|
| | | | | 165 | | | | | 170 | | | | | 175 | |

| Thr | Arg | Tyr | Glu | Leu | Gln | Glu | Phe | Leu | Gln | Asp | Thr | Cys | Val | Glu | Phe |
|---|---|---|---|---|---|---|---|---|---|---|---|---|---|---|---|
| | | | 180 | | | | | 185 | | | | | 190 | | |

| Leu | Glu | Asn | His | Ile | Thr | Thr | Gln | Asn | Met | Lys | Gly | Ser | Gln | Thr | Gly |
|---|---|---|---|---|---|---|---|---|---|---|---|---|---|---|---|
| | | | 195 | | | | | 200 | | | | | 205 | | |

| Arg | Ser | Tyr | Thr | Ser | Leu | Val | Leu | Gly | Ile | Leu | Met | Gly | Cys | Phe | Ile |
|---|---|---|---|---|---|---|---|---|---|---|---|---|---|---|---|
| | | 210 | | | | | 215 | | | | | 220 | | | |

| Ile | Ala | Gly | Val | Ala | Val | Gly | Ile | Phe | Met | Cys | Thr | Ser | Gly | Arg | Gly |
|---|---|---|---|---|---|---|---|---|---|---|---|---|---|---|---|
| 225 | | | | | 230 | | | | | 235 | | | | | 240 |

Leu Leu Ile Ile ( 2 ) INFORMATION FOR SEQ ID NO:4:

( i ) SEQUENCE CHARACTERISTICS:
        ( A ) LENGTH: 335 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Gly Cys Leu Leu Phe Leu Leu Leu Trp Ala Leu Leu Gln Ala Trp
 1               5                  10                  15
Gly Ser Ala Glu Val Pro Gln Arg Leu Phe Pro Leu Arg Cys Leu Gln
             20                  25                  30
Ile Ser Ser Phe Ala Asn Ser Ser Trp Thr Arg Thr Asp Gly Leu Ala
         35                  40                  45
Trp Leu Gly Glu Leu Gln Thr His Ser Trp Ser Asn Asp Ser Asp Thr
     50                  55                  60
Val Arg Ser Leu Lys Pro Trp Ser Gln Gly Thr Phe Ser Asp Gln Gln
 65                  70                  75                  80
Trp Glu Thr Leu Gln His Ile Phe Arg Val Tyr Arg Ser Ser Phe Thr
                 85                  90                  95
Arg Asp Val Lys Glu Phe Ala Lys Met Leu Arg Leu Ser Tyr Pro Leu
             100                 105                 110
Glu Leu Gln Val Ser Ala Gly Cys Glu Val His Pro Gly Asn Ala Ser
         115                 120                 125
Asn Asn Phe Phe His Val Ala Phe Gln Gly Lys Asp Ile Leu Ser Phe
     130                 135                 140
Gln Gly Thr Ser Trp Glu Pro Thr Gln Glu Ala Pro Leu Trp Val Asn
145                 150                 155                 160
Leu Ala Ile Gln Val Leu Asn Gln Asp Lys Trp Thr Arg Glu Thr Val
                 165                 170                 175
Gln Trp Leu Leu Asn Gly Thr Cys Pro Gln Phe Val Ser Gly Leu Leu
             180                 185                 190
Glu Ser Gly Lys Ser Glu Leu Lys Lys Gln Val Lys Pro Lys Ala Trp
         195                 200                 205
Leu Ser Arg Gly Pro Ser Pro Gly Pro Gly Arg Leu Leu Leu Val Cys
     210                 215                 220
His Val Ser Gly Phe Tyr Pro Lys Pro Val Trp Val Lys Trp Met Arg
225                 230                 235                 240
Gly Glu Gln Glu Gln Gln Gly Thr Gln Pro Gly Asp Ile Leu Pro Asn
                 245                 250                 255
Ala Asp Glu Thr Trp Tyr Leu Arg Ala Thr Leu Asp Val Val Ala Gly
             260                 265                 270
Glu Ala Ala Gly Leu Ser Cys Arg Val Lys His Ser Ser Leu Glu Gly
         275                 280                 285
Gln Asp Ile Val Leu Tyr Trp Gly Gly Ser Tyr Thr Ser Met Gly Leu
     290                 295                 300
Ile Ala Leu Ala Val Leu Ala Cys Leu Leu Phe Leu Leu Ile Val Gly
305                 310                 315                 320
Phe Thr Ser Arg Phe Lys Arg Gln Thr Ser Tyr Gln Gly Val Leu
                 325                 330                 335
```

( 2 ) INFORMATION FOR SEQ ID NO:5:

(i) SEQUENCE CHARACTERISTICS:
(A) LENGTH: 336 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Met Arg Tyr Leu Pro Cys Leu Leu Leu Trp Ala Phe Leu Gln Val Trp
 1               5                  10                  15
Gly Gln Ser Glu Val Gln Gln Lys Asn Tyr Thr Phe Arg Cys Leu Gln
                20                  25                  30
Thr Ser Ser Phe Ala Asn Ile Ser Trp Ser Arg Thr Asp Ser Leu Ile
            35                  40                  45
Leu Leu Gly Asp Leu Gln Thr His Arg Trp Ser Asn Asp Ser Ala Thr
        50                  55                  60
Ile Ser Phe Thr Lys Pro Trp Ser Gln Gly Lys Leu Ser Asn Gln Gln
 65                  70                  75                  80
Trp Glu Lys Leu Gln His Met Phe Gln Val Tyr Arg Val Ser Phe Thr
                85                  90                  95
Arg Asp Ile Gln Glu Leu Val Lys Met Met Ser Pro Lys Glu Asp Tyr
                100                 105                 110
Pro Ile Glu Ile Gln Leu Ser Thr Gly Cys Glu Met Tyr Pro Gly Asn
            115                 120                 125
Ala Ser Glu Ser Phe Phe His Val Ala Phe Gln Gly Lys Tyr Ala Val
        130                 135                 140
Arg Phe Arg Gly Thr Ser Trp Gln Arg Val Leu Gly Ala Pro Ser Trp
145                 150                 155                 160
Leu Asp Leu Pro Ile Lys Val Leu Asn Ala Asp Gln Gly Thr Ser Ala
                165                 170                 175
Thr Val Gln Thr Leu Leu Asn Asp Thr Trp Pro Gln Phe Ala Arg Gly
                180                 185                 190
Leu Leu Glu Ala Gly Lys Ser Asp Leu Glu Lys Gln Glu Lys Pro Val
            195                 200                 205
Ala Trp Leu Ser Ser Val Pro Ser Ser Ala His Gly His Leu Gln Leu
        210                 215                 220
Val Cys His Val Ser Gly Phe Tyr Pro Lys Pro Val Trp Val Met Trp
225                 230                 235                 240
Met Arg Gly Asp Gln Glu Gln Gln Gly Thr His Arg Gly Asp Phe Leu
                245                 250                 255
Pro Asn Ala Asp Glu Thr Trp Tyr Leu Gln Ala Thr Leu Asp Val Glu
                260                 265                 270
Ala Gly Glu Glu Ala Gly Leu Ala Cys Arg Val Lys His Ser Ser Leu
            275                 280                 285
Gly Gly Gln Asp Ile Ile Leu Tyr Trp Asp Ala Arg Gln Ala Pro Val
        290                 295                 300
Gly Leu Ile Val Phe Ile Val Leu Ile Met Leu Val Val Val Gly Ala
305                 310                 315                 320
Val Val Tyr Tyr Ile Trp Arg Arg Arg Ser Ala Tyr Gln Asp Ile Arg
                325                 330                 335
```

(2) INFORMATION FOR SEQ ID NO:6:

(i) SEQUENCE CHARACTERISTICS:
(A) LENGTH: 242 amino acids
(B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:6:

```
Met Leu Thr Lys Phe Leu Pro Leu Leu Leu Leu Leu Leu Pro Gly Cys
 1               5                      10                     15

Ala Leu Cys Asn Ser Asp Gly Ser Gln Ser Leu His Met Leu Gln Ile
            20                  25                  30

Ser Tyr Phe Gln Asp His His His Val Arg His Gln Gly Asn Ala Ser
        35                  40                      45

Leu Gly Lys Leu Leu Thr His Thr Leu Glu Gly Pro Ser Gln Asn Val
    50                  55                      60

Thr Ile Leu Gln Leu Gln Pro Trp Gln Asp Pro Glu Ser Trp Glu Arg
65                      70                  75                  80

Thr Glu Ser Gly Leu Gln Ile Tyr Leu Thr Gln Phe Glu Ser Leu Val
                85                      90                  95

Lys Leu Val Tyr Arg Glu Arg Lys Glu Asn Val Phe Phe Pro Leu Thr
            100                 105                 110

Val Ser Cys Ser Leu Gly Cys Glu Leu Pro Glu Glu Glu Glu Glu Gly
        115                 120                 125

Ser Glu Pro His Val Phe Phe Asp Val Ala Val Asn Gly Ser Ala Phe
    130                 135                 140

Val Ser Phe Arg Pro Lys Thr Ala Val Trp Val Ser Gly Ser Gln Glu
145                 150                 155                 160

Pro Ser Lys Ala Ala Asn Phe Thr Leu Lys Gln Leu Asn Ala Tyr Asn
            165                 170                 175

Arg Thr Arg Tyr Glu Leu Gln Glu Phe Leu Gln Asp Thr Cys Val Glu
        180                 185                 190

Phe Leu Glu Asn His Ile Thr Thr Gln Asn Met Lys Gly Ser Gln Thr
    195                 200                 205

Gly Arg Ser Tyr Thr Ser Leu Val Leu Gly Ile Leu Met Gly Cys Phe
    210                 215                 220

Ile Ile Ala Gly Val Ala Val Gly Ile Phe Met Cys Thr Ser Gly Arg
225                 230                 235                 240

Arg Cys
```